(12) United States Patent
Schmidt

(10) Patent No.: US 7,191,478 B2
(45) Date of Patent: Mar. 20, 2007

(54) SLEEPING DEVICES COMPRISING A COMBINATION OF DOWN FILLING AND A TEMPERATURE REGULATING MATERIAL

(75) Inventor: Hans Erik Schmidt, Sommersted (DK)

(73) Assignee: Quilts of Denmark A/S, Vamdrup (DK)

( * ) Notice: Subject to any disclaimer, the term of this patent is extended or adjusted under 35 U.S.C. 154(b) by 0 days.

(21) Appl. No.: 11/135,079

(22) Filed: May 23, 2005

(65) Prior Publication Data
US 2005/0262636 A1  Dec. 1, 2005

Related U.S. Application Data

(62) Division of application No. 10/755,755, filed on Jan. 12, 2004.

(51) Int. Cl.
*A47G 9/02* (2006.01)

(52) U.S. Cl. ............................... 5/502; 5/501
(58) Field of Classification Search ............ 5/502
See application file for complete search history.

(56) References Cited

U.S. PATENT DOCUMENTS

| | | | |
|---|---|---|---|
| 4,756,958 A | 7/1988 | Bryant et al. | |
| 5,290,904 A | 3/1994 | Colvin et al. | |
| 5,722,482 A * | 3/1998 | Buckley | 165/10 |
| 6,132,455 A | 10/2000 | Shang | |
| 6,210,427 B1 | 4/2001 | Augustine et al. | |
| 6,319,599 B1 | 11/2001 | Buckley | |
| 6,618,881 B2 | 9/2003 | Hart et al. | |
| 6,699,266 B2 | 3/2004 | Lachenbruch et al. | |

* cited by examiner

*Primary Examiner*—Michael Trettel
(74) *Attorney, Agent, or Firm*—Day Pitney LLP

(57) ABSTRACT

The present invention relates to a sleeping device, such as a pillow, mattress or quilt, wherein the sleeping device is adapted to be used by a person during rest and comprises a first layer of a material having temperature regulating properties and a second layer of down filling. By using a material with temperature regulating properties together with a layer of down filling, very good properties of minimizing temperature variations are obtained.

8 Claims, 2 Drawing Sheets

SLEEPING DEVICES COMPRISING A COMBINATION OF DOWN FILLING AND A TEMPERATURE REGULATING MATERIAL

CROSS-REFERENCE TO RELATED APPLICATION

This application is a division of U.S. patent application Ser. No. 10/755,755, filed on Jan. 12, 2004 and incorporated herein by reference.

FIELD OF THE INVENTION

The present invention relates to a sleeping device, such as a pillow, mattress or quilt.

BACKGROUND OF THE INVENTION

During sleep the human body goes through different phases, and in these phases the body temperature varies both as a result of internal temperature changes in the body during sleep and because of variations of the temperature in the surroundings. These temperature variations disturb the sleep. It is especially important for the sleep that the most important phase—the REM phase—is undisturbed, because in this phase the brain is recharged and prepared for the next waken period. Another effect of the temperature changes is that the quilt covering the person is kicked of during sleep, which often results in the person waking up later on freezing. Further, the temperature changes might also result in sweaty, wet sleeping devices. In both cases the temperature change does not only disturb the sleep, but might also result in sickness.

OBJECT AND SUMMARY OF THE INVENTION

It is therefore an object to provide sleeping devices solving the above mentioned problems.

This is obtained by a sleeping device, such as a pillow, mattress or quilt, wherein the sleeping device comprises a first layer of a material having temperature regulating properties adapted for minimising temperature variations and a second layer of down filling.

By using a material with temperature regulating properties together with a layer of down filling, very good properties of minimizing temperature variations are obtained. Compared to e.g. fiber filling, down filling has very good moist absorbing properties, and by minimizing the moist tests have shown that the functionality of temperature regulating materials such as e.g. phase change materials is improved considerably. Thereby the temperature regulating material can be used to fulfill the quite strict requirement to temperature variation which is necessary to get an undisturbed sleep—and especially an undisturbed REM sleep. Further, by using the temperature regulating material in the sleeping device it is avoided that the user gets sick, both because a better sleep improves the immune system and because the risk of the person unintentionally kicking of the quilt or making the sleeping devices wet because of sweat is reduced. Further, since the risk of the sleeping device getting sweaty is reduced, the frequency of which the sleeping devices and/or sleeping device covers have to be cleaned can be reduced.

In an embodiment the temperature regulating material comprises a phase change material. This material has proven to be a good material to be used in sleeping devices and can be adapted to optimally minimise the temperature variations in temperature ranges around the human body temperature.

In an embodiment the sleeping device comprises a tick defining the outer surface of the sleeping device, wherein the tick on the inside is directly followed by said first layer of temperature regulating material. Thereby the temperature regulating material is very close to the human body during use. The tick is separating the body from the temperature regulating material both in order to protect the temperature regulating material and to ensure that the down stays inside the sleeping device.

In a specific embodiment the tick defines two outer surfaces, which can be used as the surface being in contact with a user, and wherein the tick is directly followed by said first layer of temperature regulating material on the inside of one of the outer surfaces. Thereby the user can choose how much the temperature variations should be minimized. If the material is closer to the user than the down filling, then the temperature variations are smaller than when the sleeping device is turned around and the down filling is closer to the user than the temperature controlling material.

In an embodiment the tick comprising the first layer of temperature regulating material is split into channels by splitting walls. This is an easy way of designing the sleeping device, and down filling can afterwards be put Into the channels based on user needs and on around which temperature magnitude the temperature variations are to be minimized.

In an embodiment the down filling comprises goose downs. Goose down has proven to be very good at absorbing moist, whereby the functionality of the temperature regulating material is improved.

In an embodiment the sleeping device is a quilt. Thereby temperature variation around the body of the user can be minimized.

In an embodiment the sleeping device is a pillow. Thereby temperature variation around the head of the user can be minimized.

In an embodiment the sleeping device is a mattress. Thereby temperature variation around the body of the user can be minimized.

BRIEF DESCRIPTION OF THE DRAWINGS

In the following preferred embodiments of the invention will be described referring to the figures, where.

DESCRIPTION OF PREFERRED EMBODIMENTS

New materials have been developed in an attempt to address special clothing and other thermal regulating system requirements. For example, micro-encapsulated phase change materials have been described as a suitable component for substrate coatings when exceptional heat transfer and storage capabilities are desired.

In U.S. Pat. No. 5,290,904 substrates are described, which are coated with a binder containing microcapsules filled with energy absorbing phase change material. These microcapsules enable the substrate to exhibit extended or enhanced heat retention or storage properties.

Also by way of example, microencapsulated phase change materials have been described as a suitable component for inclusion in fibres, when exceptional heat transfer and storage capabilities are desired. In U.S. Pat. No. 4,756,958 a fibre with integral micro spheres filled with phase change material or plastic crystals has enhanced thermal properties at predetermined temperatures. This document further teaches that such fibres may be woven to form a fabric having the enhanced thermal storage properties.

Generally speaking, phase change materials have the capability of absorbing or releasing thermal energy to reduce or eliminate heat transfer at the temperature stabilizing range of the particular temperature stabilizing material. The phase change material inhibits or stops the flow of thermal energy through the coating during the time where the phase change material is absorbing or releasing heat, typically during the material's change of phase. This action is transient, i.e. it will be effective as a barrier to thermal energy until the total latent heat of the temperature stabilizing material is absorbed or released during the heating or cooling process. Thermal energy may be stored or removed from the phase change material, and can effectively be recharged by a source of heat or cold. By selecting an appropriate phase change material, a substrate can be coated or a fibre manufactured incorporating a phase change material for use in a particular application where the stabilization of temperatures is desired.

Figure 1:
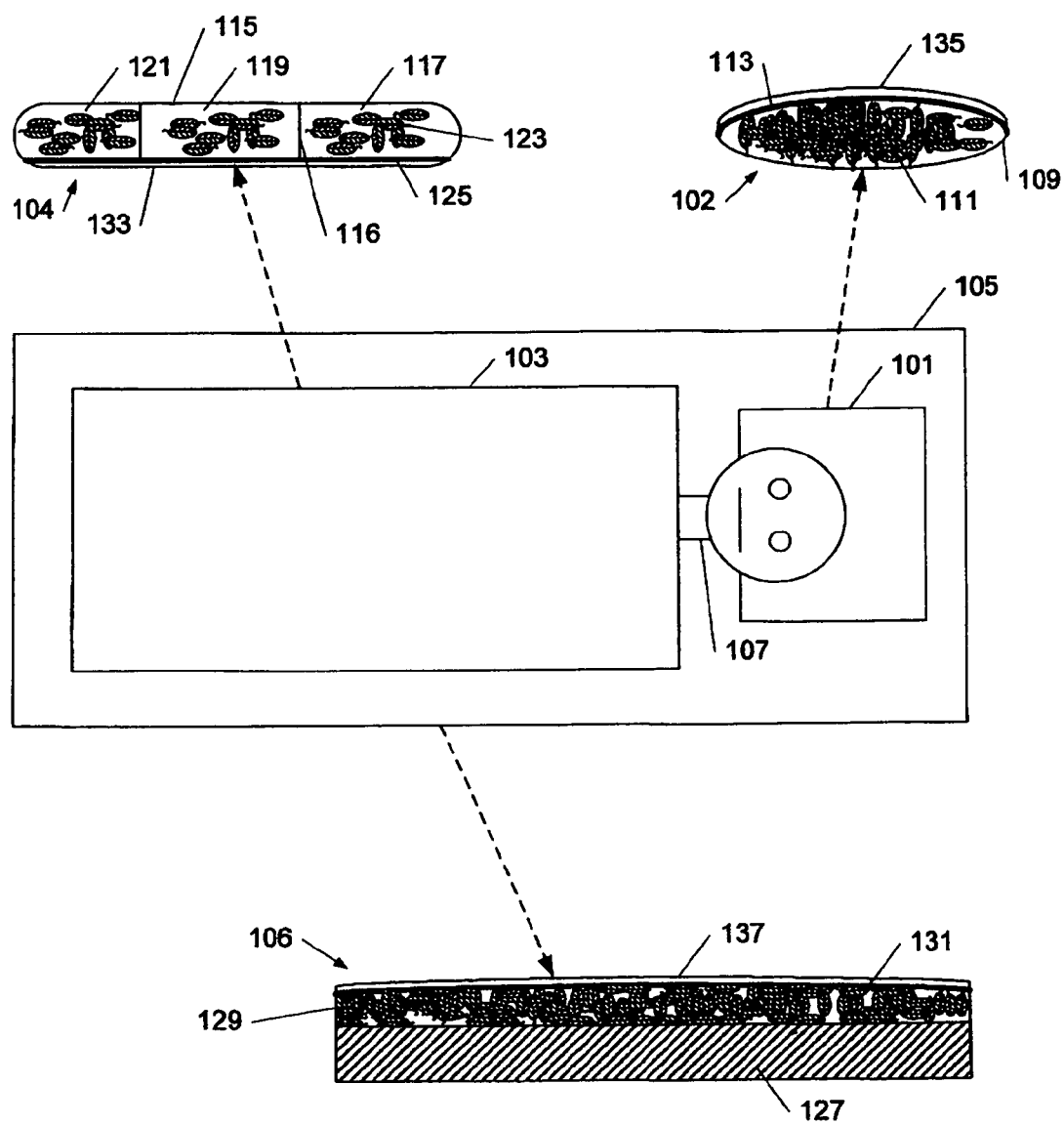
FIG. 1 illustrates sleeping devices according the present invention.

FIG. 1 Illustrates sleeping devices according to the present invention. The different sleeping devices illustrated in the figure are a pillow 101, a quilt 103 and a mattress 105 all surrounding the human body 107 during sleep. A cross section of the pillow 101 is illustrated at 102. The pillow comprises a tick 109 with down filling 111 and at least on the side pointing towards the human body a layer of temperature regulating material 113 is mounted. Another sleeping device is the quilt 103 covering the human body, a cross section of the quilt is illustrated at 104, where the quilt comprises a tick 115 with channel compartments 117, 119 and 121 and each compartment comprises down filling 123. At least on the side pointing towards the human body a layer of temperature regulating material 125 is mounted. A quilt as illustrated can be manufactured by initially sewing the tick 115 comprising the layer of temperature regulating material 125 with separating walls 116 generating channels 117, 119, 121, thereafter the down filling is blown into the channels and when filled the channels are closed. A further sleeping device is the mattress 105 on which the human body is resting; a cross section of a mattress according to the present invention is illustrated at 106, where the mattress comprises a base mattress 127 e.g. based on foam. On top of this mattress a layer of respectively down filling 129 and temperature regulating material 131 is positioned. As an alternative a top mattress to be placed on top of an existing spring based mattress could comprise the down filling and the temperature regulating material. The layer 133, 135, 137 above the temperature regulating material 113, 125, 131 ensures that the down filling stays in the sleeping device, and further the layer protects the temperature regulating layer.

The temperature regulating material could e.g. be the above described phase change material.

Figure 2:
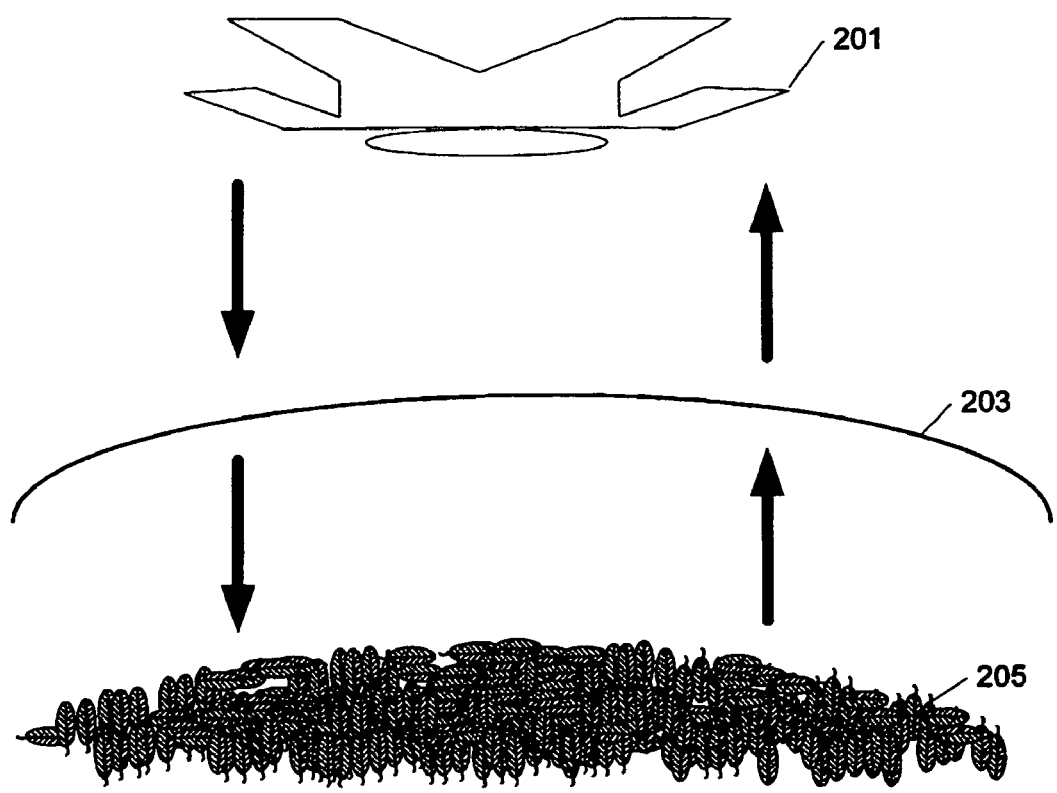
FIG. 2 illustrates the functionality of the sleeping devices according to the present invention.

In FIG. 2 the functionality of the sleeping devices according to the present Invention is illustrated. The human body is illustrated at 201, the temperature regulating material is illustrated at 203 and the down filling is illustrated at 205. When the temperature of the human body 201 increases, the extra heat is stored In the temperature regulating layer 203, and the body temperature is lowered. When the body temperature of the human body 201 decreases the stored extra heat is released from the temperature regulating layer 203, whereby the body temperature is raised. Further, the down filling being a very effective moist absorber absorbs moist from the surroundings and moist released from the human body 201. The amount of down filling is also used to ensure that the body temperature is kept at a specific magnitude, whereas the temperature regulating material is used to minimise temperature variations.

Figure 3:
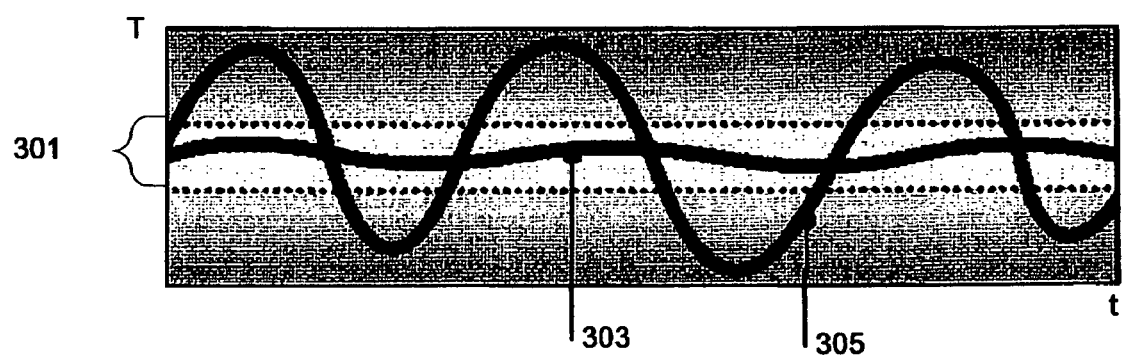
FIG. 3 illustrates the human body temperature variations when using sleeping devices according to the present invention compared to the human body temperature variations when using prior art sleeping devices.

In FIG. 3 the human body temperature variations when using sleeping devices according to the present invention are compared to the human body temperature variations when using prior art sleeping devices. On the horizontal axis is the time and on the vertical axis is the body temperature. The body temperature when using a prior art quilt is illustrated by the curve 305, whereas the body temperature when using a quilt according to the present invention is illustrated by the curve 303. Further, the interval 301 on the vertical axis is the interval defined as the optimal sleeping temperature. By using a sleeping device according to the present invention, the body temperature variations are minimised and kept within the optimal sleeping temperature interval 301, whereas when using a prior art quilt large temperature variations occur.

In the examples above the tick comprising the temperature regulating material can be sewed initially where after the tick is filled with down, where the amount of down is based on the body temperature magnitude, which the sleeping device is intended to maintain. The sleeping devices can be filled uniquely e.g. based on the climate in which the sleeping device is to be used and based on the comfort temperature of the human being intending to use the sleeping device.

In the above description sleeping devices comprising down filling are described. In this connection the word down relates to both down, feathers or a combination thereof and should therefore be interpreted correspondingly.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word 'comprising' does not exclude the presence of other elements or steps than those listed in a claim. The invention can be implemented by means of hardware comprising several distinct elements, and by means of a suitably programmed computer. In a device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sleeping device, such as a pillow, mattress or quilt, for reducing temperature variations of a human body when using said sleeping device, wherein the sleeping device comprises a first layer (113,121,131) of a material having temperature regulating properties and a second layer of down filling (111,123,129) wherein the said first layer (113, 121,131) is adapted to receive and store heat from said human body and store it when the temperature of the human body increases, and to release the stored heat from the human body when the temperature of the human body decreases.

2. A sleeping device according to claim 1, wherein the sleeping device comprises a tick (109,115) defining the outer surface of the sleeping device, wherein the tick on the inside is directly followed by said first layer of temperature regulating material (113,125).

3. A sleeping device according to claim 2, wherein the tick defines two outer surfaces, which can be used as the surface being in contact with a user, and wherein the tick is directly followed by said first layer of temperature regulating material (113,125) on the inside of one of the outer surfaces (133,135).

4. A sleeping device according to claim 2, wherein the tick comprising the first layer of temperature regulating material is split into channels by splitting wall (116).

5. A sleeping device according to claim 1, wherein the down filling comprises goose downs.

6. A sleeping device according to claim 1, wherein the sleeping device is a quilt (103).

7. A sleeping device according to claim 1, wherein the sleeping device is a pillow (101).

8. A sleeping device according to claim 1, wherein the sleeping device is a mattress (105).

\* \* \* \* \*